US010345016B2

(12) United States Patent
Garing et al.

(10) Patent No.: US 10,345,016 B2
(45) Date of Patent: Jul. 9, 2019

(54) AIR TREATMENT MODULE (71) Applicant: B/E Aerospace, Inc., Wellington, FL (US)

(72) Inventors: Francis Xavier L. Garing, Atlanta, GA (US); Alexander Nicholas Pozzi, Winston-Salem, NC (US)

(73) Assignee: B/E Aerospace, Inc., Winston-Salem, NC (US)

(*) Notice: Subject to any disclaimer, the term of this patent is extended or adjusted under 35 U.S.C. 154(b) by 56 days.

(21) Appl. No.: 15/478,790

(22) Filed: Apr. 4, 2017

(65) Prior Publication Data
US 2017/0283075 A1 Oct. 5, 2017

Related U.S. Application Data (60) Provisional application No. 62/317,693, filed on Apr. 4, 2016.

(51) Int. Cl.
*A61L 9/12* (2006.01)
*F25B 21/04* (2006.01)
(Continued)

(52) U.S. Cl.
CPC ............. *F25B 21/04* (2013.01); *A61L 9/125* (2013.01); *B64D 13/06* (2013.01);
(Continued)

(58) Field of Classification Search
CPC ... A61L 9/04; A61L 9/048; A61L 9/12; A61L 9/125; A61L 9/122; A61L 9/20; A61L 9/22; A61L 2209/11; A61L 2209/111; A61L 2209/13; A61L 2209/133; B64D 13/08; B64D 2013/0655; B64D 2013/067; B64D 2013/0688; F25B 19/04
See application file for complete search history.

(56) References Cited

U.S. PATENT DOCUMENTS

2005/0001337 A1  1/2005 Pankhurst et al.
2007/0034082 A1  2/2007 Adair et al.
(Continued)

OTHER PUBLICATIONS

Jun. 29, 2017, International Search Report for International Application No. PCT/US17/25942.

*Primary Examiner* — Timothy C Cleveland
(74) *Attorney, Agent, or Firm* — Clements Bernard Walker PLLC (57) ABSTRACT In an illustrative embodiment, an apparatus for treating air discharged to a passenger suite of an aircraft includes an enclosure that houses components for treating air passing through the enclosure and a detachable cover connected to the enclosure that provides access to the components. Air treatment components associated with air treatment flow paths within the enclosure include a blower with a fan that draws air through an air intake on the enclosure. An air duct is affixed to a discharge of the blower and directs the air discharged from the blower through an air treatment flow path that includes a scented cartridge with a scented medium that is absorbed into the air passing through the air duct. An air exhaust port is attached at a discharge end of the air duct that discharges the air conditioned by the scented cartridge through an air exhaust vent on the enclosure.

8 Claims, 8 Drawing Sheets (51) Int. Cl.
  *B64D 13/06*   (2006.01)
  *B64D 13/00*   (2006.01)
(52) U.S. Cl.
  CPC .. *B64D 2013/003* (2013.01); *B64D 2013/067* (2013.01); *F25B 2321/0251* (2013.01)

(56) References Cited

U.S. PATENT DOCUMENTS

| | | | |
|---|---|---|---|
| 2007/0178825 A1 | 8/2007 | Aronstam et al. | |
| 2008/0093474 A1* | 4/2008 | Suissa | A61L 9/122 239/34 |
| 2008/0307796 A1* | 12/2008 | Bell | F24F 5/0042 62/3.4 |
| 2011/0049259 A1* | 3/2011 | Beland | A61L 9/032 239/7 |
| 2012/0037004 A1* | 2/2012 | Ulunov | F24F 1/0003 96/371 |
| 2015/0048178 A1* | 2/2015 | Edwards | A61L 9/032 239/13 |

* cited by examiner

AIR TREATMENT MODULE

RELATED APPLICATIONS

This application claims priority to U.S. Provisional Patent Application Ser. No. 62/317,693, entitled "Air Treatment Module," filed Apr. 4, 2016. The above identified application is hereby incorporated by reference in its entirety.

BACKGROUND

Passenger airline comfort amenities often include seat features that provide adjustability and cushioning of the seat as well as seat positions for various types of activities that can include reading, eating, napping, watching videos, playing games, and working. Privacy is typically enhanced by adding partitions between suites, and in some cabin layouts dividing the seating class into a plurality of individual passenger suites. Suite features conventionally take the form of audio/video equipment, working and dining tables, stowage and lighting.

SUMMARY OF ILLUSTRATIVE EMBODIMENTS

The forgoing general description of the illustrative implementations and the following detailed description thereof are merely exemplary aspects of the teachings of this disclosure, and are not restrictive.

In certain embodiments, an air treatment module for treating air discharged to a passenger suite of an aircraft includes an enclosure that houses components for treating air passing through the enclosure and a detachable cover connected to the enclosure that provides access to the components for repair, replacement, or routine maintenance by a technician. Air treatment components associated with air treatment flow paths within the enclosure include a blower with a fan that draws air through an air intake on the enclosure. An air duct is affixed to a discharge of the blower and directs the air discharged from the blower through an air treatment flow path that includes a replaceable cartridge with a scented medium that is absorbed into the air passing through the air duct. The replaceable cartridge may be readily removed and inserted into a slot in a surface of the air treatment module, which provides for ease of swapping the scented cartridges in and out of the air treatment module due to use or passenger preference. An air exhaust port is attached at a discharge end of the air duct that discharges the air conditioned by the scented cartridge through an air exhaust vent on the enclosure. In certain embodiments, the air treatment module is configured to be inserted into a recess in the paneling of a passenger suite such that air conditioned by the air treatment module is discharged into the passenger suite. The air treatment module may be secured within the recess with locking mechanisms that are configured to prevent the air treatment module from becoming disengaged from the recess during due to movement of the aircraft. The air treatment module may be easily inserted and removed from the recess in the paneling of the passenger suite to provide for remote maintenance of the air treatment module and ease of swapping scented cartridges in and out of the air treatment module due to use of the scented cartridges or passenger preference.

In certain embodiments, the air treatment module includes a removable cover that attaches to a housing of the air treatment module to provide access to the components for inspection, repair, or replacement when the cover is removed. In some examples, the cover includes air exhaust ports for discharging conditioned air from the air treatment module.

In certain embodiments, the air treatment module includes one or more air treatment devices within the module that provide flow paths for the air drawn into the air treatment module. Each air treatment device may include a blower with a fan that draws air into the air treatment device through an air intake in the housing. In some embodiments, the fan within the blower is electrically powered and rotates at a speed based on a received passenger selection. Air drawn into the blower is discharged into an air duct that directs the air through the air treatment module. In certain embodiments, the air duct is oriented at a right angle connecting the blower to an exhaust port for the air duct.

In certain embodiments, a thermoelectric device is configured at a discharge end of the air duct for heating or cooling the air passing through the air duct based on a passenger selected temperature. The thermoelectric device may be a solid state device that uses the Peltier effect to create a heat flux between the junction of two different types of materials based on a direction and amount of current flowing through the thermoelectric device.

In certain embodiments, the air ducts include scented cartridges that have a scented medium such as a liquid or gel scented medium that is configured to emit a specific fragrance as air passes over the scented medium within the air ducts. In certain embodiments, each of the air ducts can be configured with scented cartridges having the same fragrance or different fragrances. In certain embodiments, the scented cartridges are inserted into the air treatment module as part of a cartridge module that aligns the scented cartridges within the air ducts when inserted into the air treatment module.

In certain embodiments, the air treatment module may be integrated with an aircraft cabin ventilation system such that the aircraft cabin ventilation system provides a source for the air supplied to an air intake on one side of the air treatment module.

Benefits of the embodiments described herein also include providing an individualized travel experience for travelers by providing each passenger in a premium class aircraft cabin the ability to select the scent, temperature, and other properties of the air discharged into his or her suite without affecting the travel experience of other passengers. The air treatment module also provides improved circulation around the passenger in the suite and prevents air from becoming stagnant in suites with high panels that separate the suite form the rest of the aircraft cabin.

Benefits of the embodiments described herein also include ease of access to the components of the air treatment module by removing a cover from the housing of the air treatment module so that the components can be easily inspected, repaired, and replaced as necessary. Additional benefits include that the modularity of the scented cartridges in each of the air ducts allows the scented cartridges to be easily removed and replaced so that the cartridges can be changed out as often as necessary based upon passenger selection, length of flight, or other factors.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Aspects of the present disclosure are directed to an air treatment module for conditioning air within an aircraft passenger suite, and more particularly, to an air treatment module including one or more blower fans that draw air into the suite across one or more scent sources to scent heated or cooled air within the suite. In some implementations, the air treatment module includes multiple blower fans that can be configured based on preferences of the passenger such that the passenger can select between multiple scents of air, between unscented and scented air, and between heated, cooled, or neither heated nor cooled air. In some examples, the air treatment modules may also be integrated with an aircraft cabin ventilation system such that the aircraft cabin ventilation system provides a source for the air supplied to an air intake on one side of the air treatment module. In addition, an aircraft passenger suite may include multiple air treatment modules, which increases the numbers of scents that are selectable by the passenger and allows the potency of the scent that is output by the air treatment modules to be adjusted by adjusting the number of modules that are outputting scented air.

Figure 1:
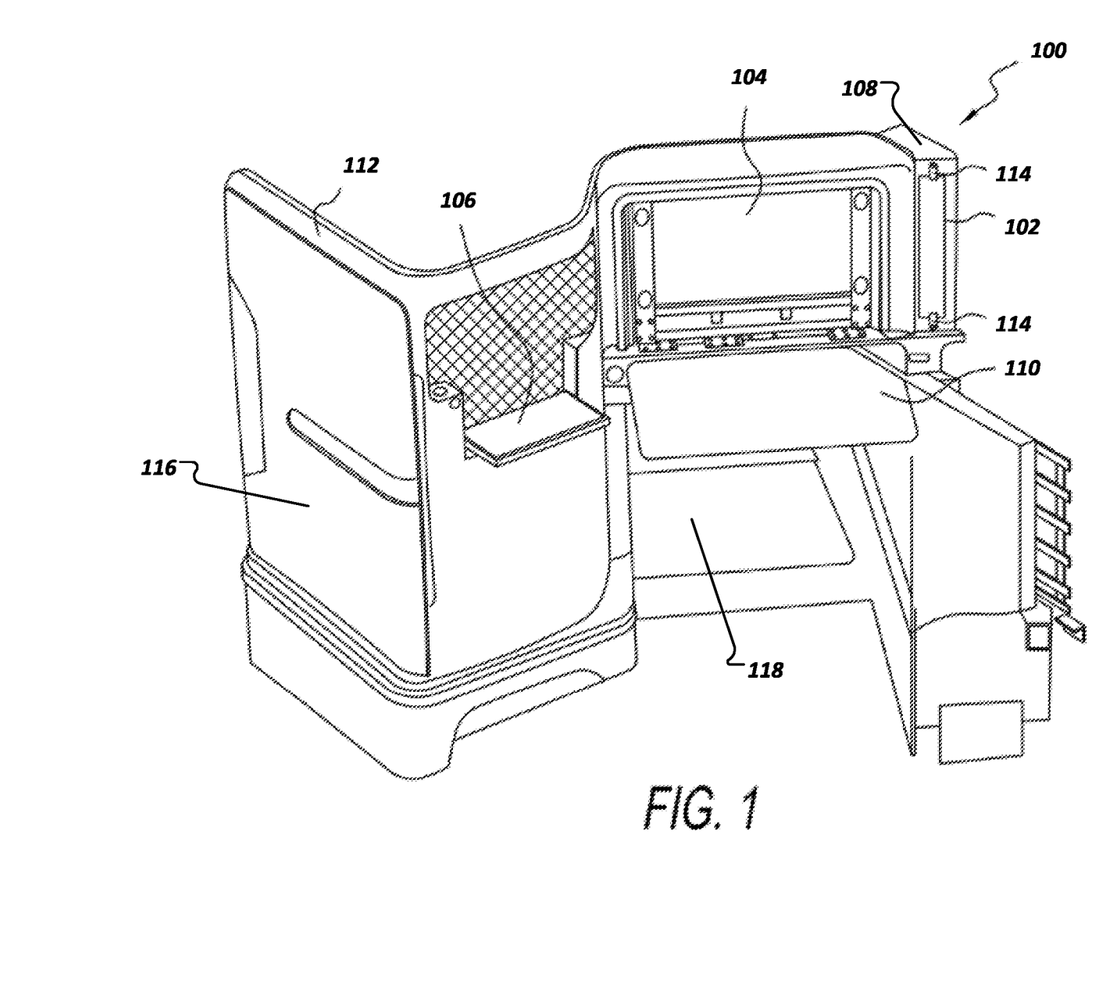
FIG. 1 illustrates a perspective view of a passenger suite including an air treatment module.

Turning to FIG. 1, an exemplary aircraft passenger suite 100 is illustrated according to some aspects of the present disclosure. In some implementations, the suite 100 may include a seat (not shown) in alignment with and facing in a direction of a video monitor 104 or other type of display device. A passenger seated in the seat faces the video monitor 104 such that the feet of the passenger in the seat are proximate a foot well 118. A primary tray table 110 may deploy directly forward of and below the video monitor 104 for use during flight for working and/or dining. A secondary table 106 may deploy to one side of the primary tray table 110 that provides an additional working surface for the passenger. In some examples, boundaries for a particular suite 100 may be defined by various partition walls 112 that extend from the floor to a height above the video monitor 104 that provide privacy for the passenger residing in the suite 100. The suite 100 may be open to an aisle on one side to allow for passenger ingress and egress from the suite 100, and can include a door 116 that slides open and closed to enhance or relax privacy. While the door 116 to the suite 100 is in the closed position, air circulating within the aircraft cabin may be at least partially blocked from entering the suite 100, which may reduce a total amount of air circulating throughout the suite 100, which may cause the suite 100 to feel uncomfortable to the passenger. The suite 100 can may also include additional features and accommodations other than those described herein that are not associated with an understanding of the implementations of the present disclosure that are described further herein.

In some implementations, to improve the air circulation throughout the suite 100, and particular when the door 116 to the suite 100 is closed, the suite 100 may further include an air treatment module 102, which as shown is positioned to one side of the video monitor 104 that can be inserted into a recess 108, which may be a hollowed-out section of a panel of the suite 100. The recess 108 may have a shape that is complementary to a shape of the air treatment module 102 such that the air treatment module 102 fits securely within the recess 108 in the suite 100. In some examples, the air treatment module 102 has a rectangular shape, and the housing 32 has a complementary rectangular recess with dimensions that correspond to the dimensions of the air treatment module 102. The recess 108 may also have a sliding mechanism such as a track that allows the air treatment module to slide smoothly into or out of the recess 108. In addition, the air treatment module 102 may have a complementary groove that rides along the track of the recess 108.

In some implementations, the recess 108 and/or air treatment module 102 may also include a securing mechanism that provides for securing the air treatment module 102 within the recess 108 such that the air treatment module remains in place within the recess 108 during turbulent or unsteady conditions within the aircraft cabin. For example, the recess 108 may include one or more hinged locking mechanisms 114 that rotate to unblock the housing recess when the air treatment module 102 is being inserted or removed from the recess 108 and similarly rotates over the recess 108 when the air treatment module 102 is inserted in the recess 108 to prevent the air treatment module 102 from sliding out of the recess 108. In other examples, the locking mechanism 114 may be a hinged flap connected to the paneling of the suite 100 that covers the recess 108 and prevents the air treatment module 102 from sliding out of the recess 108 during movement of the aircraft. The hinged flap may also include multiple perforations that allow the air conditioned by the air treatment module 102 to flow past the flap and into the suite 100. In some implementations, the paneling of the aircraft suite 100 surrounding the recess 108 may have a shape and dimensions that are complementary to the shape and dimensions of the outer surfaces of the air treatment module 102 such that the air treatment module 102 securely snaps into the paneling of the aircraft suite 100 surrounding the recess 108. In some examples, when maintenance or repair procedures are performed on the air treatment module 102, the air treatment module 102 may be easily removed from the recess 108 by an air crew member by sliding the air treatment module 102 out of the recess and replacing with another air treatment module 102 or the same air treatment module 102 when maintenance is complete. In addition, the air treatment module 102 may also be easily removed and replaced to swap scented cartridges based on passenger preferences or when used scented cartridges are replaced by with new scented cartridges.

In some examples, the recess 108 in the paneling of the suite 100 that houses the air treatment module 102 may have a rear surface including a vent or at least one aperture such that the recess 108 is at least partially open to the aircraft cabin to provide for drawing ambient cabin air through the air treatment module 102. In some implementations, the recess 108 may also include a duct connecting the foot well 118 of the suite 100 to an intake vent for the air treatment module 102 such that air is drawn from the foot well 118 into the recess 108 through the air treatment module 102. In other examples, instead of or in addition to the aperture, the recess 108 may include a connection to the aircraft ventilation system that provides air to be conditioned by the air treatment module 102. In some implementations, the air from the aircraft ventilation system may force air through air treatment module 102, causing one or more one or more blowers 314, 316 (FIG. 3A) of the air treatment module 102 to rotate.

In some implementations, the air treatment module 102 operates to condition the air within and/or provided to the suite 100. Conditioning can include, but is not limited to, heating the air, cooling the air, scenting the air, and any combinations thereof. Conditioning can be controlled by the passenger, flight crew or both via input/output (I/O) devices that connect to a controller 708 (FIG. 6) that can modify settings and configurations of the air treatment module 102 that can modify one or more settings of the air treatment module 102. In some examples, the I/O device for the air treatment module 102 is the video monitor 104 that includes a touchscreen that allows the passenger to select one or more settings for the air treatment module, which can include scent, air temperature, blower speed, humidity, etc.

While the air treatment module 102 is shown at one particular location and height, it can be understood that the air treatment module 102 may be positioned in other locations within the suite 100. For example, the air treatment module 102 may be located adjacent to an armrest or privacy panel. Further, while the suite 100 shown includes one air treatment module 102, the suite can include more than one module. For example, a second recess 108 for a second air treatment module 102 may also be configured to the left of the video monitor 104. Still further, the air treatment module 102 can be scaled larger or smaller depending upon the desired airflow output as well as the location of the air treatment module 102.

Figure 2:
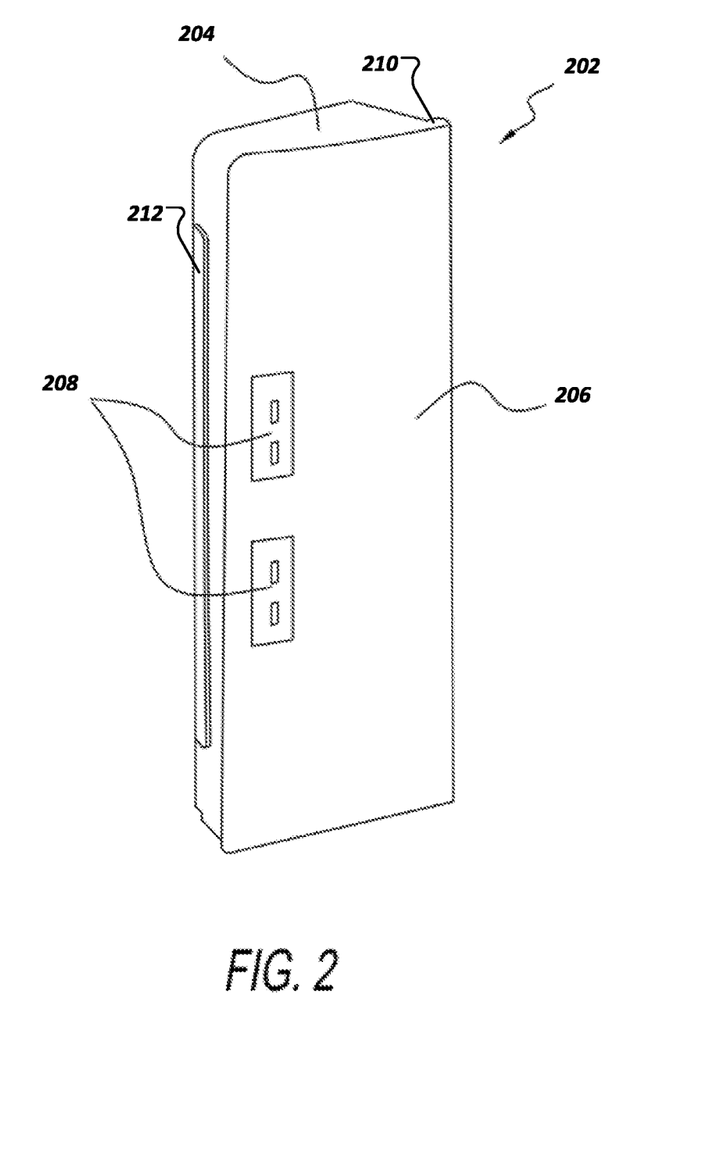
FIG. 2 illustrates a perspective view of an air treatment module with a cover attached showing exhaust ports for heated or cooled air.

FIG. 2 illustrates a perspective view of an air treatment module 202 with a cover 206 attached to a housing 204 for the air treatment module 202. The air treatment module 202 can be an implementation of the air treatment module 102 described above (FIG. 1). In some examples, the air treatment module 202 has a generally elongated, rectangular shape with a minimal thickness that is wide enough to accommodate the components of the air treatment module 202 within the housing 204. The air treatment module 202 can also have other shapes such as an elongated cylinder, cube, etc. In some implementations, the air treatment module 202 has a housing 204 for housing the components discussed in further detail below, which may be made of a strong, lightweight material such as plastic. In addition, the housing 204 may include intake vents 212 on a first surface of the housing 204 that draw air into the passenger suite 100 through vents in the recess 108 when the air treatment module 202 is inserted into the recess 108 of the suite paneling. In some implementations, the recess 108 may also include a duct connecting the foot well 118 of the suite 100 to the intake vents 212 for the air treatment module 202 such that air is drawn from the foot well 118 into the recess 108 through the air treatment module 202. In some implementations, the intake vents 212 extend along a length of the first surface of the housing 204 to provide a surface area for drawing air into the air treatment module 202. In some examples, the intake vents 212 optionally wrap around to a rear surface of the housing 204. In some implementations, the intake vents 212 include adjustable vanes that provide for adjusting a direction of air flow into the air treatment module 202 through the intake vents 212.

In some examples, cover 206 covers one side of the housing 206 so that the internal components of the air treatment module 202 are covered by the housing 204 and cover 206 when the cover 206 is connected to the housing. The cover 206 may be made of the same material as the housing 204, which in some implementations may be the same material that is used for the paneling of the aircraft suite 100 (FIG. 1). The cover 206 may be connected to the housing 204 by a hinge 210 that allows the cover 206 to fold back from the housing 204 to expose the components of the air treatment module 202 so that the internal components can be inspected, repaired, replaced, have routine maintenance performed by a technician, etc. In other examples, the cover 206 may be completely removed from the housing 204 and may detachably connect to the housing 204 by snapping to a complementary filling on the housing or sliding along a track on a connection surface with the housing 204. In alternative embodiments, the cover 206 may be optionally connected to the housing 204 when the air treatment module 202 is inserted into the recess of the passenger suite 100.

In some implementations, the cover 206 may include a pair of spaced ports 208 through which conditioned air can be exhausted. The ports 208 provide an exhaust path for conditioned air circulated through the air treatment module 202. In some examples, the air treatment module 202 may be inserted into the recess 108 of the passenger suite 100 such that the cover 206 is facing outward into the passenger suite 100, and a primary path for conditioned air into the passenger suite 100 is through the exhaust ports 208 in the cover 206 of the air treatment module 202. The exhaust ports 208 may also include vents that provide for directing the conditioned air in a desired direction and/or blocking the conditioned air from exiting through the exhaust ports 208.

Figure 3A:
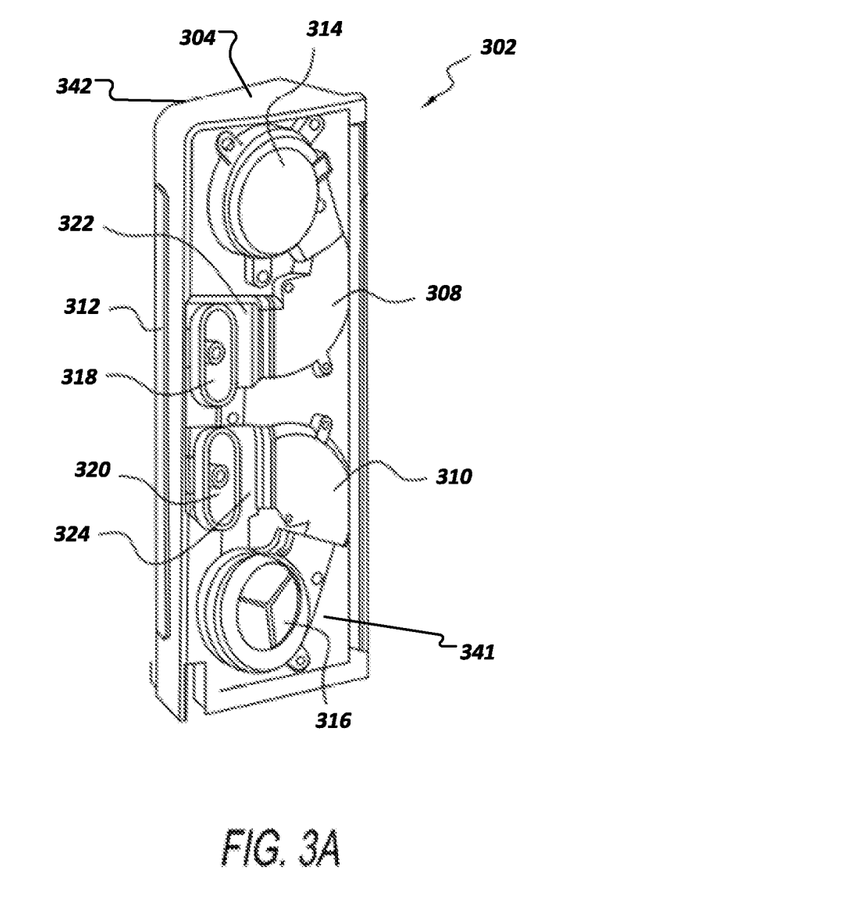
FIG. 3A illustrates a perspective view of an air treatment module shown with a cover removed to reveal the internal blowers and thermoelectric devices.

FIG. 3A illustrates a perspective view of an air treatment module 302 with the cover removed. As described above, the air treatment module 302 may include a housing 304 that houses the internal components of the air treatment module 302 that condition the air that is drawn into the air treatment module 302. In some examples, the air treatment module 302 has a generally elongated, rectangular shape with a minimal thickness that is wide enough to accommodate the components of the air treatment module 302 within the housing 304. In addition, a first surface of the housing 304 may include intake vents 312 that draw air into the passenger suite 100 through vents in the recess 108 when the air treatment module 302 is inserted into the recess 108 of the passenger suite 100. In some implementations, the recess 108 may also include a duct connecting the foot well 118 of the suite 100 to the intake vents 312 for the air treatment module 302 such that air is drawn from the foot well 118 into the recess 108 through the air treatment module 302. In some implementations, the intake vents 312 extend along a length of the first surface of the housing 304 to provide a surface area for drawing air into the air treatment module 202. In some examples, the intake vents 312 optionally wrap around to a rear surface 342 of the housing 304 for provide additional surface area for drawing air into the housing 304.

Figure 4:
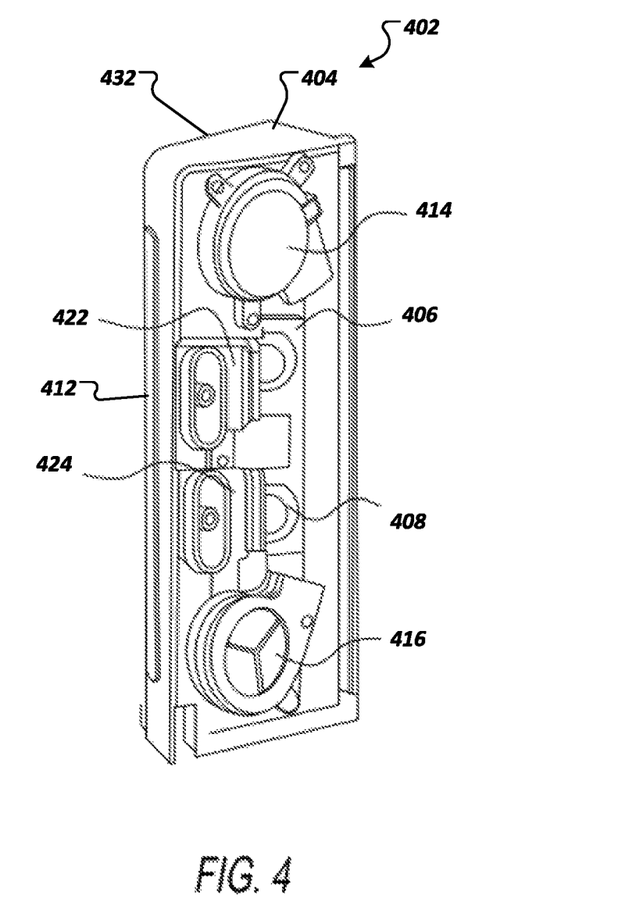
FIG. 4 illustrates a perspective view of an air treatment module shown with the cover, intermediate wall, and ducting removed to reveal the scented cartridges exposed to the air flow.

In some implementations, the air treatment module 302 includes one or more air treatment devices that can condition air based on preferences of the passenger (type of scent, unscented or scented air, and heated, cooled, or neither heated nor cooled air, etc.). For example, the air treatment module 302 includes first and second air treatment devices with respective blowers 314, 316, ducts 308, 310, thermoelectric devices 322, 324, exhaust ports 318, 320, and scented cartridges 406, 408 (FIG. 4). In other examples, the air treatment module 302 may include a single air treatment device or greater than two air treatment devices.

In addition, the arrangement of the components of the air treatment devices within the housing 304 may be based on the number and size of the air treatment devices, configuration of the air treatment module 302 within the passenger suite 100 and other design factors. In some examples, first and second fan blowers 314, 316 may be positioned near respective ends of the air treatment module 302. In some implementations, the air treatment module 302 includes an intermediate wall 341 to which the internal components of the air treatment module are affixed. The intermediate wall may run parallel to the rear surface 342 of the housing 304 such that a gap exists between the rear surface 342 of the housing 304 and the intermediate wall 341. In some examples, air drawn into the air treatment module 302 through the air intake vents 312 and into the gap between the rear surface 342 of the housing 304 prior to entering the blowers 314, 316. In some examples, a width of the gap between the rear surface 342 of the housing 304 and the intermediate wall 341 corresponds to a width of the air intake vents 312.

In some implementations, the blowers 314, 316 may include electrically driven fans that can rotate at variable speeds in either direction based on a user setting. In some examples, the direction of rotation of the fans in the blowers 314, 316 is based on an orientation of the ducts 308, 310 and exhaust ports 318, 320 within the housing 304. For example, the fan for the blower 314 may rotate in a direction that is opposite the direction of rotation of the fan for the blower 316 due to the opposite facing orientations of the ducts 308, 310 and exhaust ports 318, 320 from one another within the housing 304. As the speed of rotation of the fans increase, the speed and amount of air passing through the air treatment module 302 increases, which can increase the amount of conditioned air output into the passenger suite 100.

In some examples, the fans for the blowers 314, 316 may not have any electrical connections and may be mechanically driven in response to an external air supply being forced through the intake vents 312 causing the fans within the blowers 314, 316 to rotate as the air supply contacts the blades of the fans. For example, in implementations where the aircraft cabin ventilation system provides a supply of air to the air treatment module 302, the air from the ventilation system may force air through air treatment module 302, causing the fans within the blowers 314, 316 to passively activate by forcing rotation of the fan blades. As the passenger modifies an amount of cooling or force of air output by the air treatment module 302, the temperature, force, and/or volume of air output by the ventilation system to the intake vents 312 may be adjusted. For example, an aperture leading from the ventilation system to the air treatment module 302 may be adjusted based upon a desired force or volume of air output.

Exterior air drawn in through the first and second blowers 314, 316 through the exterior air intake may be directed through respective first and second ducts 308, 310. The first and second ducts 308, 310 may be right-angled and direct air from the respective blowers 314, 316 over scented cartridges 406, 408 (see FIG. 4) and ultimately through respective first and second exhaust ports 318, 320. In some examples, the shape and orientation of the first and second ducts 308, 310 is based on locations of the other components of the air treatment devices with respect to one another within the housing 304 and can have other shapes than the right-angled bend shown in FIG. 3A. For example, the ducts 308, 310 may be straight or have bend angles that are greater or less than 90 degrees.

In some implementations, first and second thermoelectric devices 322, 324 may be located at downstream ends of the first and second ducts 308, 310 and adjacent to the first and second exhaust ports 318, 320, in other examples, the thermoelectric devices 322, 324 may be located at other locations such as upstream of the first and second ducts 308, 310 and adjacent to the first and second blowers 314, 316. The thermoelectric devices 322, 324 can operate to heat or cool the air depending on the desired output temperature. In some implementations, the thermoelectric devices 322, 324 may be solid state heating/cooling devices that are configured to cool or heat the conditioned air by using the Peltier effect to create a heat flux between the junction of two different types of materials based on a direction and amount of current flowing through the thermoelectric devices 322, 324. One example of the thermoelectric devices 322, 324 can be thermoelectric cooling modules made by the Tellurex Corporation in Traverse City, Mich., but any type of thermoelectric device can be used that can heat or cool the conditioned air to a predetermined temperature range. In some implementations, the predetermined temperature range can include any temperature between 60 degrees and 80 degrees Fahrenheit, but wider or narrower temperature ranges can also be used. The conditioned air can be heated, cooled, or neither heated nor cooled by the thermoelectric devices 322, 324 based on a current supplied by a controller 708 (FIG. 6) that receives a passenger temperature input from an I/O device.

In an alternate embodiment, the thermoelectric devices 322, 324 may not be included in the air treatment module 302. For example, the air treatment module 302 may not include any electrical connections, such as in the case of the passively activated fans for the blowers that are mechanically driven in response to air from the aircraft ventilation system being forced through the intake vents 312 causing the fans within the blowers 314, 316 to rotate as the supplied contacts the blades of the fans. In addition, instead of using the thermoelectric devices 322, 324 to heat or cool the supplied air, the temperature of the supplied air can be modified by the ventilation system in response to a received input. As the passenger adjusts settings for an amount of heating or cooling or force of air output by the air treatment module 302, the temperature, force, and/or volume of air output by the ventilation system to the intake vents 312 may be adjusted.

Conditioned air can be exhausted through the first and second exhaust ports 318, 320 in the front of the air treatment module 302. In some implementations, the first and second exhaust ports 318, 320 may be oriented toward the exhaust ports 208 in the cover 206 (FIG. 2) for the air treatment module 302. In addition, the vents on the exhaust ports 208 of the cover 206 can be adjusted to angle the airflow and/or increase or decrease the flow of conditioned air into the passenger suite 100.

Figure 3B:
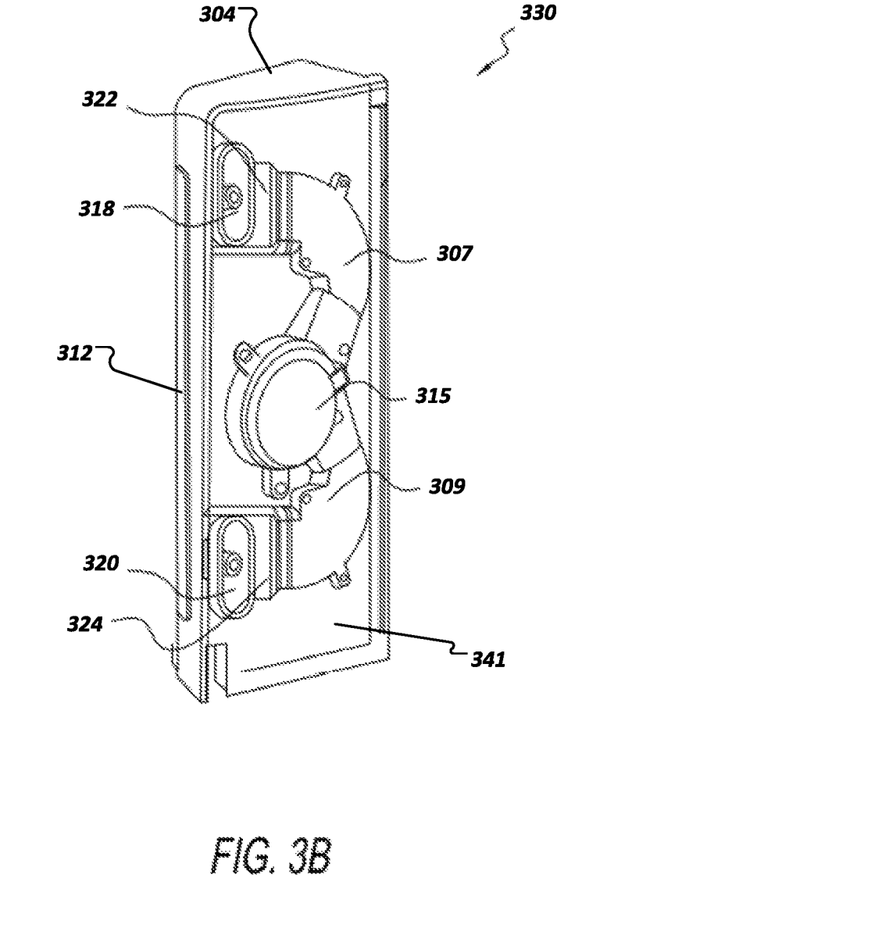
FIG. 3B illustrates a perspective view of an air treatment module having a single blower with two blower ducts.

FIG. 3B illustrates an alternate implementation of an air treatment module 330 that includes a single blower 315 that supplies air drawn into the air treatment module 330 through the intake vents 312 to first and second ducts 307, 309 that are connected to the blower 315 and further to first and second thermoelectric devices 322, 324 and first and second exhaust ports 318, 320. In addition, the blower 315 may be positioned substantially in the center of the housing 304 of the air treatment module 330 with the first and second ducts 307, 309 branching out away from the blower 315 at right angles toward the ends of the air treatment module 304 such that the first and second exhaust ports 318, 320 may be located adjacent to the ends of the housing 304.

In some implementations, incoming air may be directed through the first duct 307 or the second duct 309 based on a direction of rotation of the fan in the blower 315. For example, when the fan rotates in a clockwise direction, incoming air may be directed through the second duct 309. Similarly, when the fan rotates in a counterclockwise direction, air may be directed through the first duct 307. In some examples, each duct 307, 309 includes differently scented cartridges 406, 408 or one scented and one unscented cartridge, which provides for selection of a first scent associated with the first scented cartridge 406 or a second scent associated with the second scented cartridge 408 based on the direction of rotation of the fan of the blower 315.

Turning to FIG. 4, a perspective view of an air treatment module 402 is illustrated with a cover 206, ducts 308, 310, and intermediate wall 341 removed to reveal first and second scented cartridges 406, 408. The scented cartridges 406, 408, provide scent sources for the air flowing through the air treatment module 402 and can be positioned in the gap between the intermediate surface 341 and rear surface 432 of housing 404 such that air drawn into the housing 404 through the intake vents 412 and into the blowers 414, 416 flows over and around the scented cartridges 406, 408 and wicks the scent away from the scented cartridges 406, 408 so that the air flowing through the ducts 308, 310 becomes scented. In addition, the scented air flowing through the ducts 308, 310 can be heated or cooled by thermoelectric devices 422, 424 and exits the ducts 308, 310 through first and second exhaust ports 418, 420. The effect of the configuration of the scented cartridges 406, 408 within the air treatment module 402 is that the scent is wicked from the scented cartridges 406, 408 and exhausted into the area of the passenger suite 100 to change the scent of the immediate air around the passenger.

In some implementations, the scented cartridges 406, 408 may be removable and replaceable modules that can include a scented medium such as a liquid or gel scented medium that is configured to emit a specific fragrance as air passes over the scented medium, however, other types of scented media can also be used. Non-limiting examples of fragrances associated with the scented media of the scented cartridges 406, 408 may include orange, lemon, caraway, cedar, geranium, lavender, rose, and the like. In some implementations, the scented cartridges 406, 408 in each of the ducts 308, 310 may have the same fragrance or different fragrances. In addition, one or both of the ducts 308, 310 may have scented cartridges 406, 408 that do not include a scented medium so that the air passing across the cartridges without the scented medium remains unscented. In other examples, one or both of the ducts 308, 310 may not have scented cartridges 406, 408 installed such that slots in the air treatment module 402 where the scented cartridges 406, 408 are inserted remain empty. In some implementations, the slots where scented cartridges 406, 408 are inserted may be cutouts on one side of the ducts 308, 310 having a shape that corresponds to the shape of the scented cartridges 406, 408 such that the air flowing through the ducts 308, 310 is exposed to the scented media of the scented cartridges 406, 408 as air flows through the ducts 308, 310.

In some examples where each of the ducts 308, 310 include scented cartridges 406, 408 with different scents or one of the ducts 308, 310 includes a scented cartridge and the other duct includes an unscented cartridge or an empty cartridge slot, the type of scent emitted by the air treatment module 402 is selectable by a passenger at an input device, such as video monitor 104 (FIG. 1). For example, if the duct 308 includes scented cartridge 406 having a lavender scent and duct 310 includes scented cartridge 408 having a lemon scent, then the passenger can select whether the lavender scent or the lemon scent is output by the air treatment module 402 to the passenger suite 100. If the lavender scent is selected, then the controller 708 (FIG. 6) outputs control signals to turn on the fan in blower 414 for duct 308 and turn off the fan in blower 416 for duct 310 so that the incoming air travels only through the duct 308 with the scented cartridge 406 having the lavender scent. Similarly, if the lemon scent is selected, then the controller 708 outputs control signals to turn off the fan in blower 414 for duct 308 and turn on the fan in blower 416 for duct 310 so that the incoming air travels only through the duct 310 with the scented cartridge 408 having the lemon scent.

Figure 5:
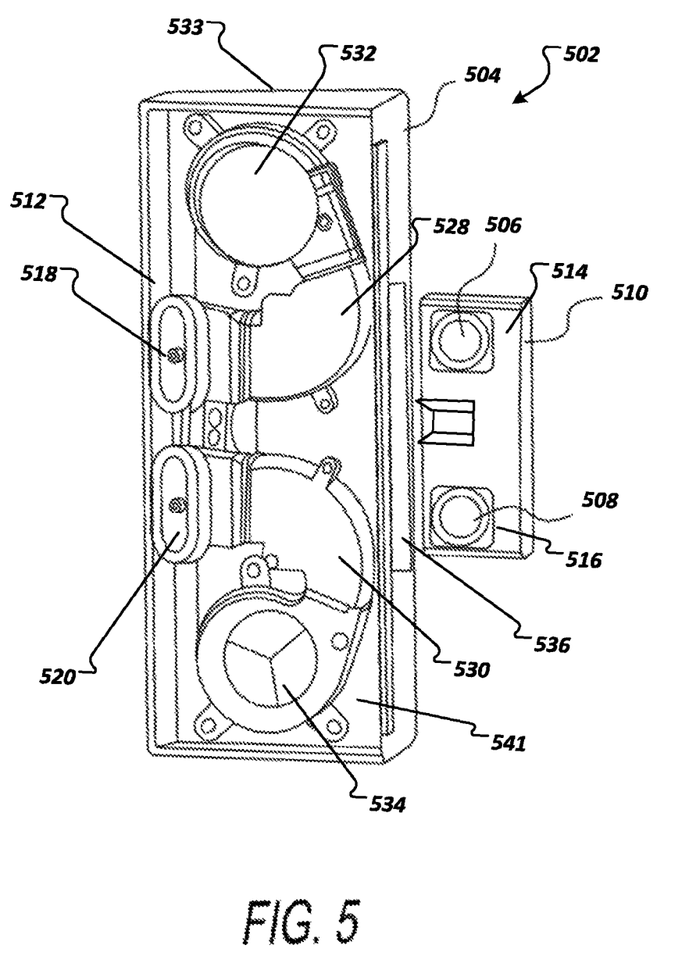
FIG. 5 illustrates a perspective view of the air treatment module showing the scented cartridge removed from the module.

Turning to FIG. 5, a perspective view of air treatment module 502 is shown with scented cartridges 506, 508 removed from the air treatment module 502. In an example, the air treatment module 502 may include first and second ducts 528, 530, first and second blowers 532, 534, first and second exhaust ports 518, 520, intake vents 512, as well as any other components described in the implementations above. In some implementations, the scented cartridges 506, 508 can be included as part of a cartridge module 510 that houses the scented cartridges 506, 508 in cartridge compartments 514, 516 that correspond to each of the ducts of the air treatment module 502. For example, for the air treatment module 502 having two ducts, the cartridge module 510 includes two compartments 514, 516. The cartridge compartments 514, 516 may house scented cartridges 506, 508 having the same scent, different scents, or are unscented.

In addition, the dimensions of the cartridge module 510 and locations of the cartridge compartments 514, 516 within the module 510 may be based on the dimensions of the housing 504, and the spacing of the components of the air treatment module 502 within the housing 504. For example, a cartridge module 510 for the air treatment module 330 (FIG. 3B) with the single blower 315 with the ducts 307, 309 extending away from the edges of the housing 304 may have a longer length than a cartridge module 510 for the air treatment module 302 (FIG. 3A) s with two blowers 314, 316 each having ducts 308, 310 extending toward the center of the housing 304 because a distance between the ducts 307, 309 for the air treatment module 330 may be greater than a distance between the ducts 308, 310 for the air treatment module 302. In some examples, the cartridge module 510 may be configured with a single cartridge compartment to hold a single scented cartridge such that individual cartridge modules are inserted into each of the ducts of the air treatment module 502.

In some implementations, the cartridge module 510 may slide in and out of a slot 536 disposed on a rear surface of the housing 504 for the air treatment module 502, similarly to the movement of a drawer. In some implementations, the slot 536 may be aligned with a gap between intermediate surface 541 and rear surface 533 of the housing 504 such that the cartridge module is inserted through the slot 536 and into the gap between the rear surface 533 of the housing 504 and the intermediate surface 541. The cartridge module 514 may be readily removed and inserted into the slot 536, which provides for ease of swapping the scented cartridges in and out of the air treatment module 502 due to use or passenger preference.

Figure 6:
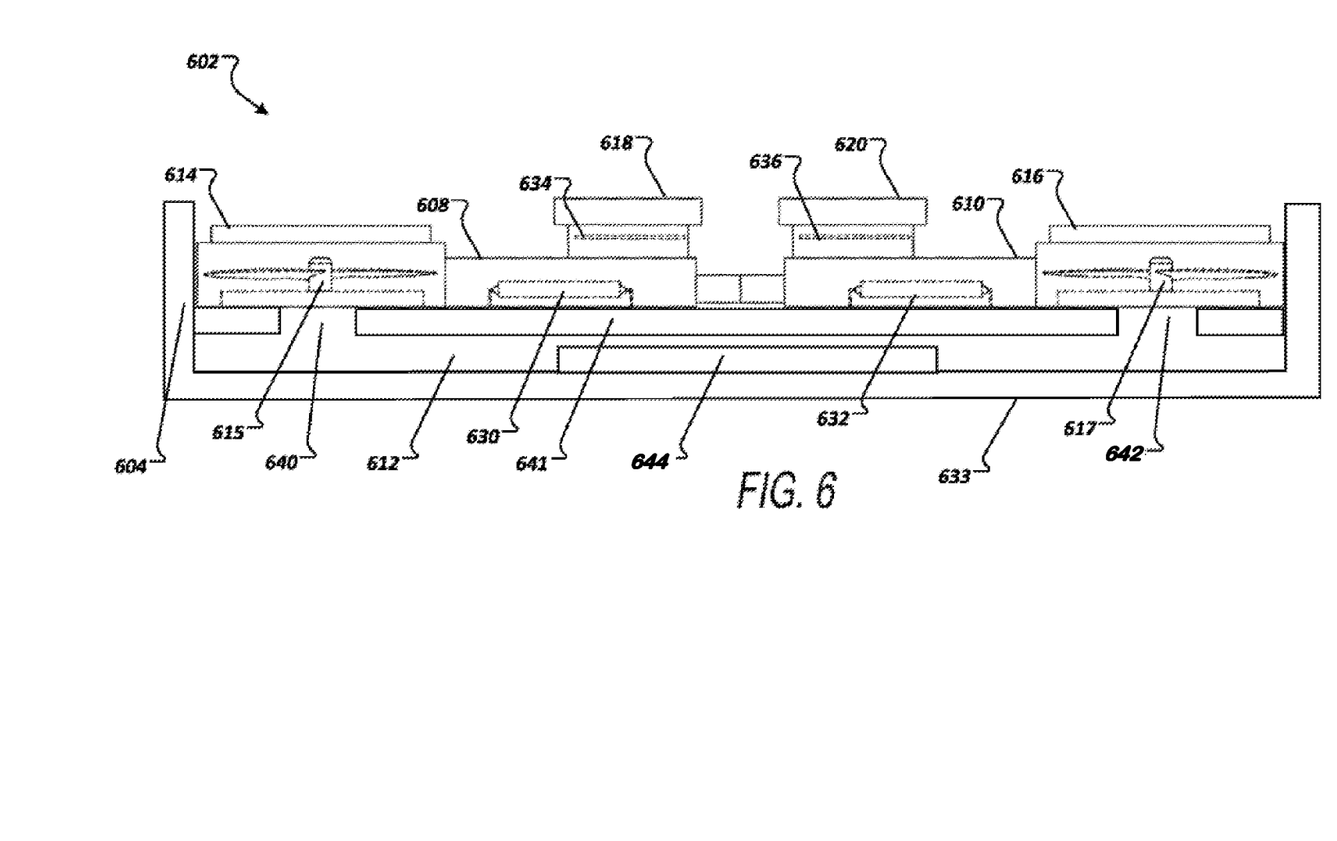
FIG. 6 illustrates a sectional view of an air treatment module.

For example, FIG. 6 illustrates a sectional view of an air treatment module 602 showing a gap 612 between the rear surface of housing 604 and an intermediate surface 641 of the air treatment module 602 that runs parallel to the rear surface 633. In some examples, the gap 612 is aligned with the intake vents 312 (FIG. 3A) of the air treatment module 602 such that air drawn into the air treatment module 602 through the intake vents enters the gap 612. In some examples, cartridge module 644 can be inserted into the gap 612 through a slot 536 (FIG. 5) in the housing 604 of the air treatment module 602. In some aspects, the cartridge module 644 includes scented cartridges 406, 408 that provide scent sources for the air flowing into air treatment module 602 such that air drawn into the housing 604 through the intake vents 312 and into blowers 614, 616 through apertures 640, 642 in the intermediate wall 641 flows over and around the scented cartridges 406, 408 disposed within the cartridge module 644 and wicks the scent away from the scented cartridges 406, 408 so that the air flowing through the ducts 608, 610 becomes scented.

In addition, any of the components illustrated in FIG. 6 may be included in any of the implementations described above. In some implementations, the internal components 600 may include includes blowers 614, 616 with electrically driven fans 615, 617 that can rotate at variable speeds in either direction based on a user input to draw air into the air treatment module. The air drawn into the blowers 614, 616 may be discharged to ducts 608, 610 that direct the air passing through the air treatment module toward first and second exhaust ports 618, 620 and into the passenger suite. In some implementations, the each of the ducts 608, 610 may include respective air purifiers 630, 632 that remove impurities from the air drawn into the air treatment module. For example, the air purifiers 630, 632 may be ultraviolet (UV) light purifiers, ionization purifiers, or any other type of air purification device. In addition, the air purifiers 630, 632 may be electrically controlled components that can be turned on or off remotely by a passenger or aircrew member at an I/O device, such as the video monitor 104 (FIG. 1).

In addition, each of the ducts 608, 610 may include respective first and second scent sensors 634, 636 that can detect the scent of the scented cartridges 506, 508 (FIG. 5). The scent sensors 634, 636, in some embodiments, are configured to detect a unique code disposed upon a scent cartridge to identify the scent loaded into the corresponding duct 608, 610. The scent sensors 634, 636 for example, may include an image sensor for detecting a bar code, QR code, or other machine-readable indicia indicative of a particular scent cartridge. The machine readable indicia, for example, may be translated into a particular scent by the controller. In other embodiments, the scent sensors 634, 636 may be configured to read a radio frequency (RF) label to identify the particular scent of the cartridge. For example, the scent sensors 634, 636 may be configured to wirelessly communicate with a passive RF antenna of a scent cartridge to receive product information, and detect within the product information the scent. Alternatively, the scent sensors 634, 636 may retrieve the product information from the passive RF antenna and supply the information to the controller 708 for analysis. In further embodiments, the scent sensors 634, 636 can detect the scent of a scented medium that has been absorbed into the air passing through the ducts 608, 610. The scent sensors 634, 636 may be any type of sensor that is capable of detecting scents or generating signal patterns that correspond to specific scents, which may include MOSFET devices, conducting polymers, polymer composites, quartz crystal microbalance, or surface acoustic wave (SAW) micro electromechanical systems (MEMS). In one example where the scent sensors 634, 636 are MOSFET devices, molecules in the air associated with different scents that enter the sensor area affect the electric field of the MOSFET devices differently, generating output signals from the MOSFETs that are distinguishable from other scents. The output signals from the MOSFETs are sent to the controller 708 (FIG. 7), which analyzes the output signal patterns to determine which scent is associated with each of the sensors 634, 636. In some implementations, the controller 708 outputs the detected scents associated with each of the ducts 608, 610 to the video monitor 104 (FIG. 1) with an indication to contact the flight attendant if the passenger wishes to have another type of scented cartridge installed within the air treatment module.

Figure 7:
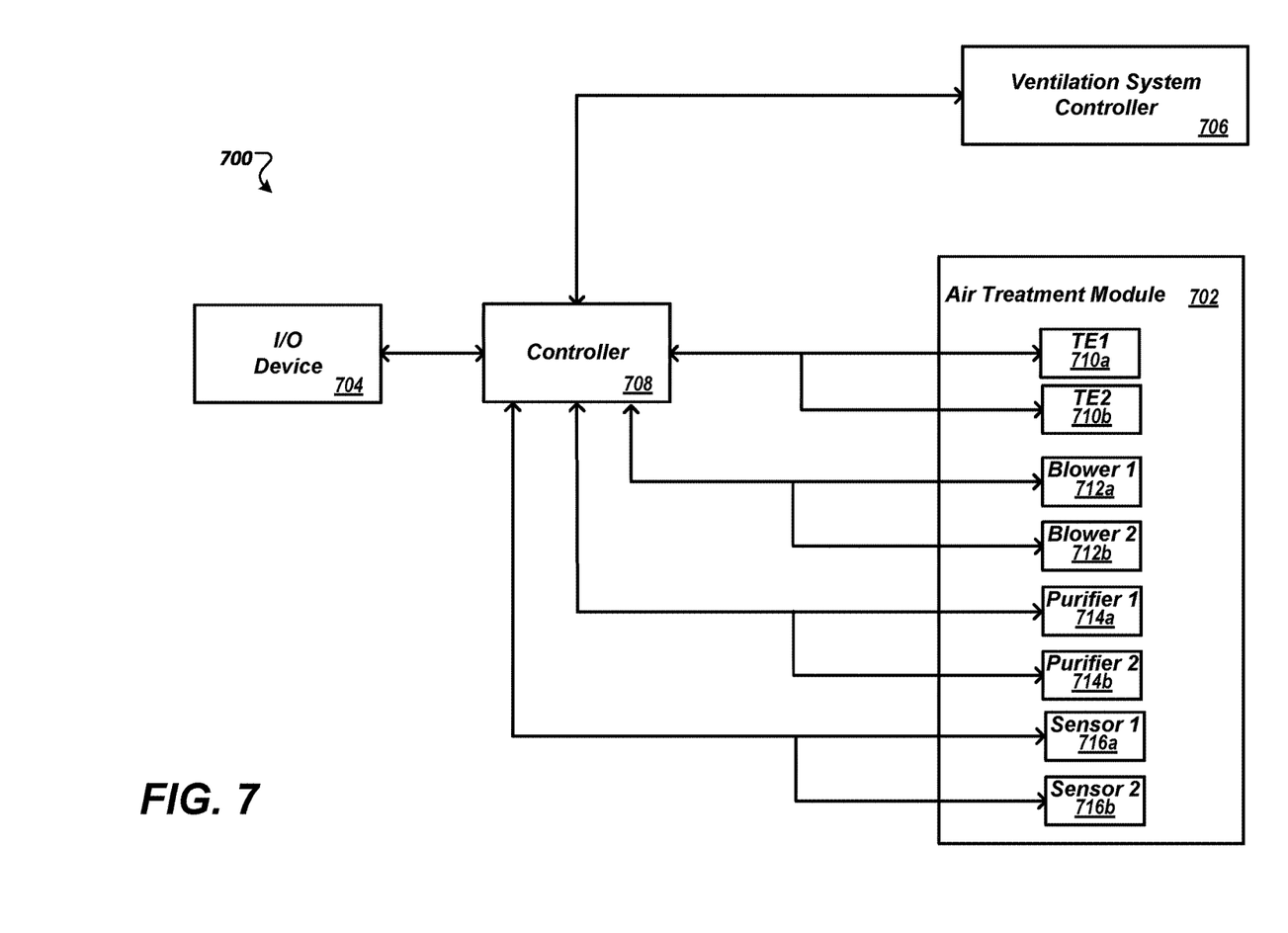
FIG. 7 illustrates a diagram of electrical connections to the air treatment module.

Turning to FIG. 7, a diagram 700 showing electrical connections to electrical components of an air treatment module is illustrated. In some implementations, the air treatment module 702 includes electrically powered components such as first and second thermoelectric devices (TE1 and TE2) 710, electrically driven fans in blowers 712, air purifiers 714, and scent sensors 716. The electrical components of the air treatment module 702 can be remotely controlled by a controller 708 based on passenger selections received at an input/output (I/O) device 704, which may be the video monitor 104 (FIG. 1) within a passenger suite 100 where the passenger can select settings for the air treatment module 702 that can include type of scent, air temperature, fan speed, number of operating fans, and the like.

The controller 708 may be any type of controller device such as a programmable logic controller, that receives the selections from the I/O device and translates the selections into control signals to adjust settings of the thermoelectric devices 710, blowers 712, purifiers 714, and/or scent sensors 716. The controller 708 may include a processor, memory, and other associated circuitry may have a wired or wireless connection to the I/O device 704. For example, if a passenger requests an increase in fan speed of the blowers 712 at the I/O device 704, then the controller 708 outputs a control signal to the blowers 712 to modify the fan speed to correspond to the request. Similarly, if the passenger requests a reduction in air temperature output by the air treatment module 702. The controller 708 can adjust a supply current to the thermoelectric devices 710 so that the temperature of the conditioned air output by the air treatment module 702 conforms to the requested temperature. The passenger can also remotely turn on or off the air purifiers 714 from the I/O device 704. Once the thermoelectric devices 710, blowers 712, and/or purifiers 714 have reached a state that corresponds to the inputs, the controller 708 outputs a current state of the air treatment module 702 based on the adjustments to the thermoelectric devices 710, blowers 712, and/or purifiers 714 to the I/O device 704. In addition, the air treatment module 702 may include other electrical component configurations than that shown in FIG. 7.

In some implementations, the controller 708 may receive output signals from sensors 716 that have output signal patterns corresponding to specific scents. The controller 708 can analyze the output signal patterns by comparing the patterns to a database of signal patterns for various scents that are stored in memory of the controller 708. In some implementations, the controller 708 outputs the detected scents associated with each of the ducts to the I/O device 704 with an indication to contact the flight attendant if the passenger wishes to have another type of scented cartridge installed within the air treatment module.

In some implementations, the controller 708 may be electrically connected to an aircraft cabin ventilation system controller 706 in implementations where the ventilation system supplies air to the air treatment module 702. For example, when the aircraft cabin ventilation system provides a supply of air to the air treatment module 702, the air from the ventilation system may be forced through the air treatment module 702, causing the fans within the blowers to rotate. As the passenger modifies an amount of cooling or force of air output by the air treatment module 702, the temperature, force, and/or volume of air output by the ventilation system air treatment module 702 may be adjusted.

The air treatment module described in the implementations above provides an individualized travel experience for travelers by providing each passenger in a premium class aircraft cabin the ability to select the scent, temperature, and other properties of the air discharged into his or her suite without affecting the travel experience of other passengers. The air discharged into the passenger suite from the air treatment module improves circulation within the passenger suite and helps prevent the air within the suite from becoming stagnant due to high panels that separate the suite from the rest of the cabin. In addition, the removable cover of the air treatment module provides ready access to the components of the air treatment module so that the components can be easily inspected, repaired, and replaced as necessary. Also, the modularity of the scented cartridges in each of the air ducts allows the scented cartridges to be easily removed and replaced so that the cartridges can be changed out as often as necessary based upon passenger selection, length of flight, or other factors. By making the scented cartridges modular, scents may be customized for an airline, per route, per time frame, per carrier, by passenger, etc.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A system for treating air within a passenger suite of an aircraft, the system including an air treatment module comprising:
   an enclosure,
   an air intake aperture disposed on a first surface of the enclosure,
   a blower including a fan configured to draw air through the air intake aperture,
   a first duct having a first end connected to the blower for directing air from the blower through a first flow treatment path within the enclosure to a first exhaust port for discharging air into the passenger suite,
   a second duct having a first end connected to the blower for directing air from the blower through a second flow treatment path within the enclosure to a second exhaust port for discharging air into the passenger suite,
   a removable first cartridge containing a first scented medium having a first scent, the first cartridge disposed in the first flow treatment path such that the first medium is absorbed into air passing through the first flow treatment path to the first exhaust port, a removable second cartridge containing a second scented medium having a second scent, the second cartridge disposed in the second flow treatment path such that the second medium is absorbed into air passing through the second flow treatment path to the second exhaust port, and control circuitry comprising processing circuitry, and a non-transitory computer readable medium having instructions stored thereon, wherein the instructions, when executed by the control circuitry, cause the control circuitry to     receive a selection of the first scent or second scent from a computing device, and     rotate the fan in a first rotational direction to direct air into the first duct if the first scent is selected thereby causing the first scented medium to be absorbed into air passing through the first flow treatment path to the first exhaust port, and     rotate the fan in a second rotational direction opposite the first rotational direction to direct air into the second duct if the second scent is selected thereby causing the second scented medium to be absorbed into air passing through the second flow treatment path to the second exhaust port.

2. The system of claim 1, wherein, the control circuitry rotates the fan at a variable speed based on a user setting.

3. The system of claim 1, further comprising a drawer for removing and replacing at least one of the removable first cartridge and removable second cartridge.

4. The system of claim 1, wherein at least one of the first air treatment flow path and second air treatment flow path includes an air purifying component, and the air purifying component comprises an ultraviolet light purifier.

5. The system of claim 1, further comprising a thermoelectric device for modifying a temperature of air prior to discharge via the first exhaust port or second exhaust port.

6. The system of claim 1, wherein the selection is received wirelessly from a touch screen interface disposed proximate a passenger seat of the passenger suite.

7. The system of claim 6, wherein the control circuitry is further configured to receive, from at least one scent sensor, indication of the first scent of the first scented medium contained in the removable first cartridge, and provide, for presentation to a passenger via the touch screen interface, the indication of the first scent.

8. The system of claim 1, wherein the enclosure is designed to be releasably received within a track disposed in a partition of the passenger suite.

\* \* \* \* \*